United States Patent [19]

David et al.

[11] Patent Number: 4,633,177

[45] Date of Patent: Dec. 30, 1986

[54] DEVICE FOR CHECKING BENT TUBES BY A PROBE, SUCH AS A PNEUMATICALLY PROPELLED EDDY-CURRENT PROBE

[75] Inventors: Bernard David, Gif sur Yvette; Michel Pigeon, Bures sur Yvette; Claude Vienot, Fontenay-sous-Bois, all of France

[73] Assignee: Commissariat a l'Energie Atomique, Paris, France

[21] Appl. No.: 570,652

[22] Filed: Jan. 13, 1984

[30] Foreign Application Priority Data

Jan. 18, 1983 [FR] France ............................ 8300692

[51] Int. Cl.⁴ ................... G01N 27/87; G01R 33/12; B65H 51/00; G21C 17/00
[52] U.S. Cl. ................................ 324/220; 226/171; 376/249
[58] Field of Search .................. 324/219–221; 73/622, 623; 376/249, 254; 226/170, 171, 172

[56] References Cited

U.S. PATENT DOCUMENTS

| | | | |
|---|---|---|---|
| 2,048,754 | 7/1936 | Putnam | 226/171 |
| 3,100,070 | 8/1963 | Smith | 226/171 |
| 4,087,748 | 5/1978 | Pigeon et al. | 324/220 |
| 4,179,056 | 12/1979 | Schmerling | 226/171 |
| 4,262,539 | 4/1981 | Jamison et al. | 73/622 |
| 4,494,907 | 1/1985 | Coussau et al. | 324/220 X |

FOREIGN PATENT DOCUMENTS

| | | |
|---|---|---|
| 0026701 | 4/1981 | European Pat. Off. . |
| 2320542 | 3/1977 | France . |
| 2339231 | 8/1977 | France . |

OTHER PUBLICATIONS

Chashi et al; "Research . . . of the Method of Inserting Probe into Helically Coiled Tubes . . . for In-Service Inspection"; IHI Engineering Rev., vol. 13, No. 1, Jan. 1980, pp. 1–6.

Primary Examiner—Gerard R. Strecker
Attorney, Agent, or Firm—James E. Nilles

[57] ABSTRACT

A device for checking bent tubes by means of a probe, such as a pneumatically propelled eddy-current probe. The device comprises a sealing-tight enclosure adapted to communicate with the tube to be checked via a connecting tube. The introduction pressure of the probe is produced by a pneumatic circuit. The probe comprises a checking head and a cable having floaters and is wound on a coil driven by a torque motor. The introduction speed of the probe is controlled by passing it over a drive pulley, to which it is permanently applied by a strap tensioned by a spring, the pulley being mounted on the shaft of a constant-speed motor. Application to the checking of the tubes of heat exchangers, condensers and steam generators, more particularly of nuclear reactors.

11 Claims, 4 Drawing Figures

DEVICE FOR CHECKING BENT TUBES BY A PROBE, SUCH AS A PNEUMATICALLY PROPELLED EDDY-CURRENT PROBE

The invention relates to a device for checking curved, more particularly helical, and inter alia metal tubes for heat exchange in apparatuses such as steam generators and condensors.

BACKGROUND OF THE INVENTION

More precisely, the invention relates to a device for checking curved tubes which enables a probe, such as an eddy-current probe, to be propelled pneumatically inside the tubes in order to check their condition. The fact is that the detection and localization of faults are essential checking operations in heat exchange apparatuses, more particularly when there is a risk that the two fluids will react with one another, as is the case in steam generators associated with liquid-metal-cooled nuclear reactors, in which the two fluids are respectively sodium and water. Faults liable to rupture a tube must therefore be detected as quickly as possible, so as to prevent them from getting worse and avoid the very serious consequences which might result both for the plant and the environment.

To this end a certain number of tube checking devices are already known. We may cite more particularly the device described in the article "Research and Development of the Method of Inserting Probe into Helically Coiled Tubes in Steam Generator for In-Service Inspection (ISI)" published in the Review IHI Engineering Review, vol. 13, No. 1 which enables a probe to be introduced pneumatically into a tube, by attaching the probe to a cable having floaters, the introduction of the cable into the tube being facilitated by a suitable guide mechanism which at the same time seals off the pneumatic propulsion system from the exterior.

French Pat. No. 2,320,542 of Aug. 7, 1975, in the name of the Commissariat a l'Energie Atomique discloses an eddy-current probe connected by a cable having suitable guide means, such as floaters, to the device enabling it to be introduced into the tube and extracted from the tube.

These prior art devices enable the probe to be introduced into a bent tube having small-radius bends and welding beads. However, they do not wholly satisfactorily solve the problem posed by the pneumatic introduction of the probe, which results in an excessive and highly irregular speed of probe movement, more particularly when a very long tube is being checked (for example, about 100 m). The speed of movement of the probe must therefore be reduced and regularized, so that it remains substantially constant from one end to the other of the tube to be checked.

PROBLEM OF THE INVENTION

The pneumatic introduction of the probes by the prior art method also had the disadvantage of causing jerks and vibrations, which frequently broke the cable to which the probe was attached. In view of the structure of the prior art probes and cables, it was therefore very difficult to extract the probe from the tube again. The invention not only regularizes the movement of the probe, thus tending to reduce the risks that the cable will break, but also aims at providing a probe and cable whose structure enables the cable to be recovered even if it breaks.

BRIEF STATEMENT OF THE INVENTION

The invention therefore provides a device for checking curved, more particularly helical tubes, using a pneumatically propelled probe, comprising a sealing-tight enclosure adapted to communicate with a tube to be checked, means for introducing a pressurized fluid into the enclosure and evacuate the fluid from the enclosure, a probe comprising a cable having floaters and a sensing head attached to the end of the cable, and cable-winding means, wherein the device also comprises means for controlling the introduction speed of the probe which are disposed inside the sealing-tight enclosure and comprise a decelerating device of constant, controlled speed connected for corotation to the shaft of a pulley formed with a groove through which the cable extends, means being provided for applying the cable to the pulley, whatever the section of the cable may be, such means comprising a belt permanently tensioned by resilient means and adapted to be deformed in accordance with the section of the cable.

In a first embodiment of the invention the decelerating device comprises a motor with electronically controlled speed.

In a second embodiment of the invention, the deceleration device comprises an electromagnetic brake whose braking torque is controlled electronically.

In a preferred embodiment of the invention, means are provided for transmitting the rotation of the pulley to the belt, so as to make the belt advance at the same speed as the groove in the pulley.

Preferably, to ensure the permanent tensioning of the cable between its winding coil and the means for regulating the introduction speed, the cable-winding means comprise a coil mounted on the shaft of a torque motor.

So as to prevent the probe from getting jammed in the tube when it starts to be introduced, the floaters can be spaced out from one aother by at least two different steps along the cable, the steps separating the floaters nearest to the sensing head being less than and, for example, half the step which separates the other floaters.

To enable the probe to be recovered, even if it breaks, as already stated, the probe comprises over its whole length a central pulling cable which extends through the sensing head and is attached to the front end thereof. The attachment can more particularly be carried out by means of a knot coated with a gluing material, thus preventing the internal surfaces of the tube from being scored by the strands of the central cable.

In parallel, and in order to increase the resistance to breakage of the connection between the cable and the sensing head, such connection can be made by means of a spring in which there are electrical connections between coaxial electric conductors of the cable and windings of the sensing head, such spring being filled with a filling material, such as a supple resin.

BRIEF DESCRIPTION OF DRAWINGS

By way of non-limitative example, two embodiments of the invention will now be described with reference to the accompanying drawings, wherein.

DESCRIPTION OF PREFERRED EMBODIMENTS

The device according to the invention is particularly well adapted to the inspection by means of an eddy-current probe, of very long bent tubes, such as the helically wound tubes of a steam generator associated with a liquid-metal-cooled nuclear reactor. However, it will be understood that the device might also be used to inspect tubes of any other nature by means of a probe operating by a different principle.

Figure 1:
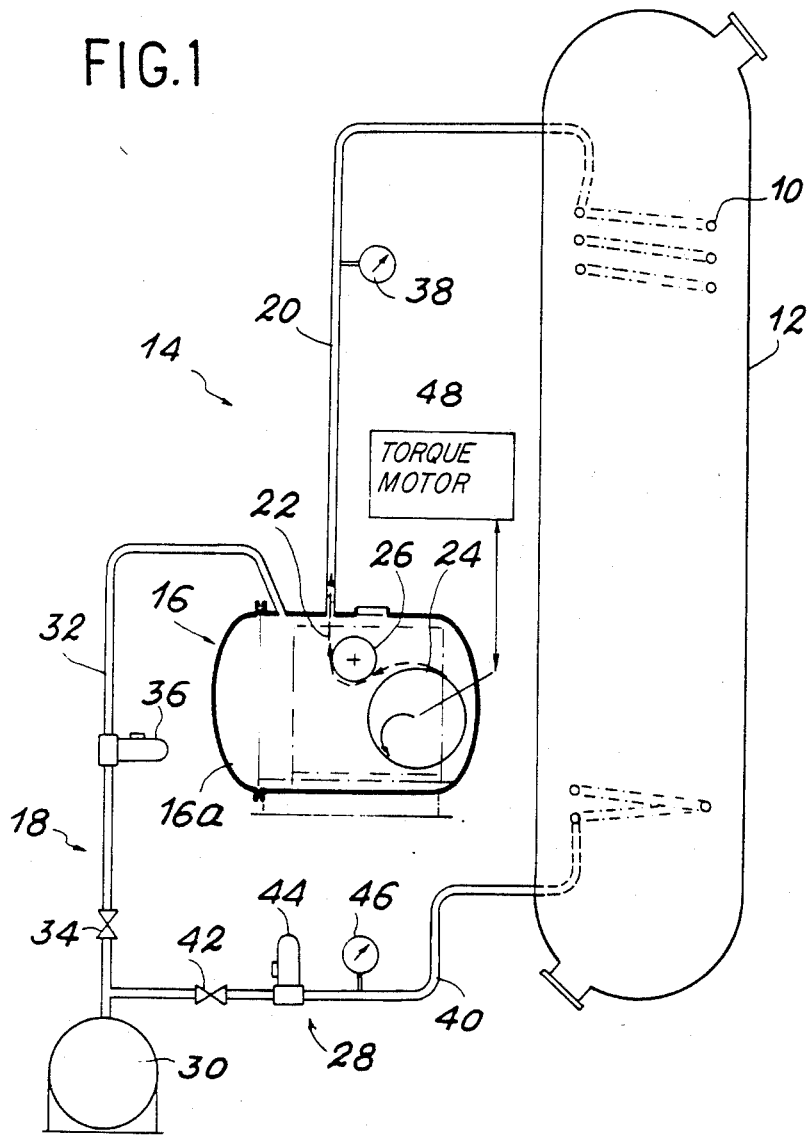
FIG. 1 is a diagrammatic sectional view of the checking device according to the invention

To illustrate the preferred application of the invention to checking the tubes of a steam generator, FIG. 1 shows diagrammatically one of the helically wound tubes 10 of a steam generator 12.

Steam generators associated more particularly with fast neutron nuclear reactors are familiar to specialists, so that the steam generator 12 will not be described in detail. To understand the invention, it is enough to know that each of the tubes 10 extends through the vertical envelope of the generator and discharges at its bottom and top ends into inlet and outlet collectors (not shown) of, for example, toroidal shape. The structure of these collectors or of parts of tubes lying between the collectors and the exchange envelope is such that access can be had to each of the tubes to introduce a probe into them by means of a checking device such as device 14 according to the invention.

As shown diagrammatically in FIG. 1, the inspection device 14 mainly comprises a sealing-tight enclosure 16, means 18 for introducing a pressurized fluid, such as compressed air, into the enclosure 16, a flexible tube 20 by means of which the enclosure 16 and the tube 10 to be checked are in sealing-tight communication, a probe 22 comprising, as will be disclosed hereinafter, a sensing head and a connecting cable 23 (FIG. 2), a coiler 24 and means 26 for regulating the speed of introduction of the probe into the tube to be checked, the coiler 24 and the means 26 being disposed inside the sealing-tight enclosure 16, and means 28 for applying a counterpressure to the other end of the tube 10 to be checked, so as to return the probe to the inside of the enclosure 16 when the check is completed.

Preferably, to ensure the maintenance of the different mechanisms inside the enclosure 16, the latter has a gate 16a provided with a completely sealing-tight closure mechanism.

The compressed air which introduces the probe into the tube to be checked and brings the probe out of the tube is produced by a compressor 30, communicating with the enclosure 16 via a pipe 32 having a valve 34 and a discharge valve 36. These various elements from the means 18 for introducing compressed air into the sealing-tight enclosure 16, thus ensuring the pneumatic introduction of the probe 22 into the tube 10 to be checked, when the connecting tube 20 is connected sealing-tight to the top end of the tube 10 (as viewed in FIG. 1). Preferably, the pressure for introducing the probe thus set up at the inlet to the tube 10 is checked by means of a manometer 38 connected to the connecting tube 20. Comparably, the means 28 for bringing the probe out of the tube 10 comprise a duct 40 via which the compressor 30 communicates sealing-tight with the bottom end of the tube 10, the duct 40 having a valve 42 and a discharge valve 44. Preferably, the duct 40 comprises a resilient portion which enables it to be readily connected to the bottom end of the tube 10. A manometer 46 is also provided in the duct 40 to control the pressure in the duct, more particularly when the probe returns to the enclosure 16.

As shown more particularly in FIG. 2, the probe 22 comprises a sensing head 25 which will be described hereinafter (FIG. 3) and a cable 23 whose length is at least equal to the length of the tube to be checked. At rest the cable is wound in a coil 24a on a coiler 24, the coiler being mounted on the shaft of a torque motor 48 (FIG. 1) of known kind when the checking device 14 is put into operation. Due to the inherent characteristics of the torque motor, a constant tensioning is applied to the cable 23 of the probe between the coil 24a and the introduction speed regulating means 26, whatever the speed of displacement given to the probe may be, even when the probe remains immobile.

Figure 2:
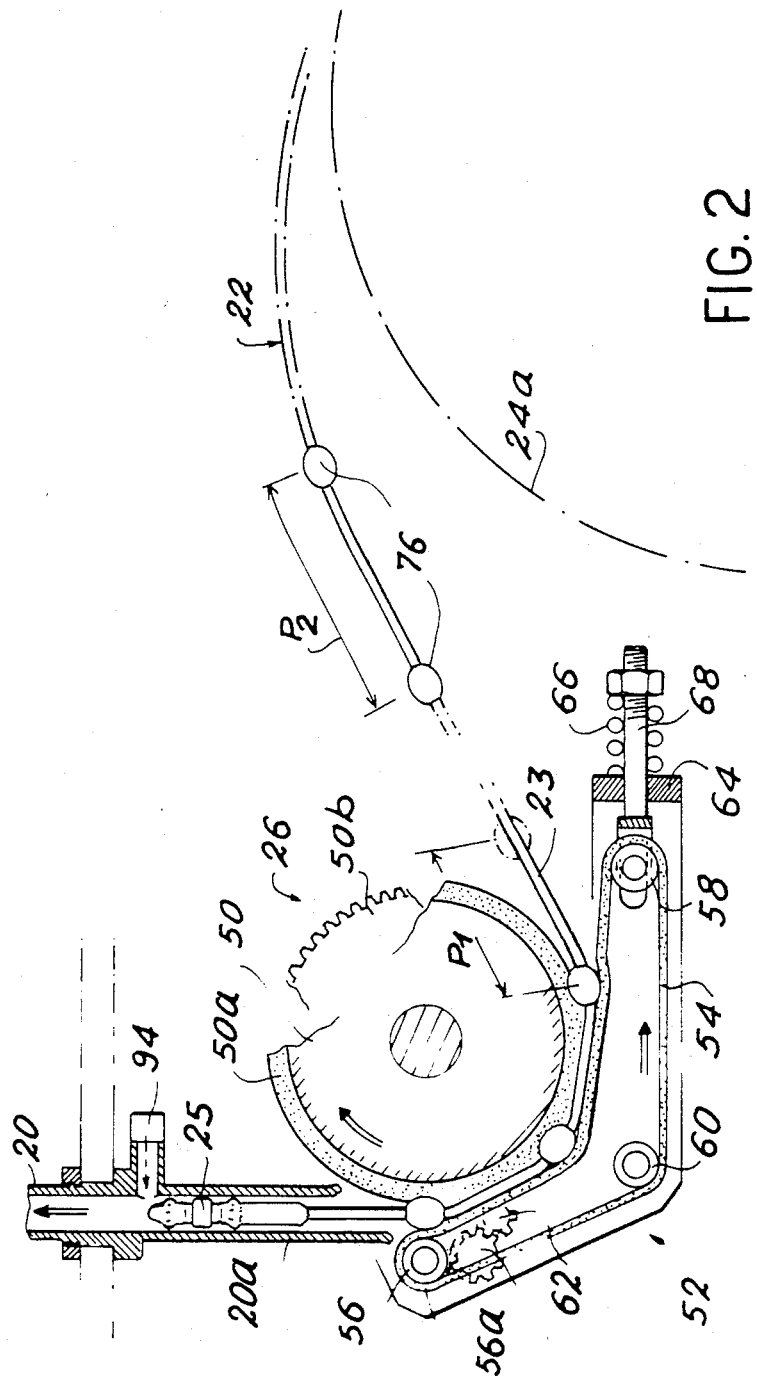
FIG. 2 is a sectional view, to an enlarged scale, of the device enabling the speed of introduction of the probe into the tube to be regulated.

FIG. 2 also shows how the means 26 for regulating the speed of introduction of the probe comprise a pulley 50, whose axis is parallel with the axis of the coil 24a, and means 52 for maintaining the cable 23 in the groove in the pulley, so as to ensure that the cable is entrained by the pulley despite variations in the cross-section of the cable, which will be described hereinafter.

The shaft of the pulley 50 is rotatably connected to a d.c. electric motor (not shown) whose speed is controlled electronically. Although the motor rotates in the direction corresponding to the introduction of the probe into the tube, it behaves like a decelerating device acting against the compressed air for introducing the probe, in order to regulate the speed at which the probe is introduced into the tube. A motor of substantially constant speed would also enable the movement of the probe in the tube to be checked to be controlled under the action of the compressed air. The motor can be regulated automatically, either by a tachymetric dynamo, or by means of a pulse encoder.

The periphery of the pulley 50 is formed with a V-shaped groove 50a in which the cable 23 is kept engaged by means 52.

Such means 52 comprise a belt 54 or any equivalent device adapted to apply the cable 23 to the groove in the pulley and to be deformed in order to take on the shape of the cable. The endless belt 54 is received on rollers, as 56, 58 and 60. More precisely, the rollers 56 and 58 are so disposed that the part of the belt 54 lying between them curves inwardly to take on the shape of the cable 23 and maintain the latter in that part of the groove 50a in the pulley which precedes a part 20a of the connecting tube 20 lying inside the envelope 16. The roller 56 closest to the part 20a of the tube ensures the entrainment of the belt 54 at a speed equal to the peripheral speed of rotation of the pulley 50 at the level of the groove 50a. To this end the pulley 50 is connected to a toothed wheel 50b, the roller 56 is connected to a pinion 56a, and a set of pinions 62 ensures the suitable step-down and transmission of the rotary motion of the toothed rim 50b to the pinion 56a.

Moreover, means for tensioning the belt 54 are provided so as to keep the part of the belt for applying the cable to the pulley permanently tensioned, even though the cross-section of the cable varies. These tensioning means are disposed between the roller 58 and a fixed member 64. More precisely, these are formed by a compression spring 66 acting between the fixed member 64 and a shoulder formed on a mobile member 68 supporting the spindle of the roller 58 via the agency of a spur-shaped part.

The probe 22 which, as has been seen, is made up of a sensing head 25 and a cable 23 will now be described in greater detail with reference to FIGS. 2 and 3.

The cable 23 serves at one and the same time to ensure the mechanical connection between the device 26 for regulating the speed of introduction of the probe and the sensing head, and also for ensuring the transmission of the electric signals between the eddy-current coils of the sensing head and the electronic means (not shown) which in known manner enable the coils to be supplied and the signals which they deliver to be processed, so as to supply the required information concerning the state of the walls of the checked tubes.

To this end the cable 23 comprises, starting from the centre, pulling cable 70 made of a strong material, such as Kevlar (registered trade mark), three coaxial electric conductors 72a, 72b and 72c and an external protective sheath 74 of an insulating plastic material, on which olive-shaped protuberances or floaters 76 are moulded at regular intervals. The external diameter of the floaters 76 is so calculated as to be slightly less than the internal diameter of the tube 10 to be checked, even in the zones where the latter has a slight constriction due, for example, to the presence of a weld. These floaters ensure the guiding of the cable inside the tube and allow a uniform distribution of the thrust exerted by the compressed air when the probe is introduced.

The sensing head 25 mainly comprises a central part 78, in which the eddy-current coils are mounted, and a front guiding part 80 and rear guiding part 82.

More precisely, the central part 78 comprises two annular measuring coils 84a and 84b and a saturation winding 84c, the coils and winding being enclosed in a block of resin. The front 80 and rear 82 centering members mainly comprise a resilient ring of, for example, rubber. The external diameter of the rings is determined in the same way as the external diameter of the floater 76, in order to ensure the guiding of the sensing head 25 inside the tube 10 to be checked, while allowing the passage of the sensing head in the parts of the tube having slight constrictions of diameter. Moreover, the front centering member 80 has on the front face of the resilient guiding ring an ogival member 86 determining the front end of the sensing head 25.

The external diameter of the part 78 bearing the eddy-current coils is smaller than the external diameter of the resilient guiding parts 80 and 82 and so calculated that the distance separating the coils from the walls of the tube to be checked enables the required measurements to be carried out in satisfactory conditions. For example, for a tube of 19.7 mm in diameter, the diameter of the parts 80 and 82 can be 20.2 mm, and that of the part 78 can be 18 mm.

The resilient connection between the three parts 78 and 80 and 82 of the sensing head is made by means of a helical spring 88 whose ends are attached to the centring members 80 and 82 and which support the central part 78.

Figure 3:
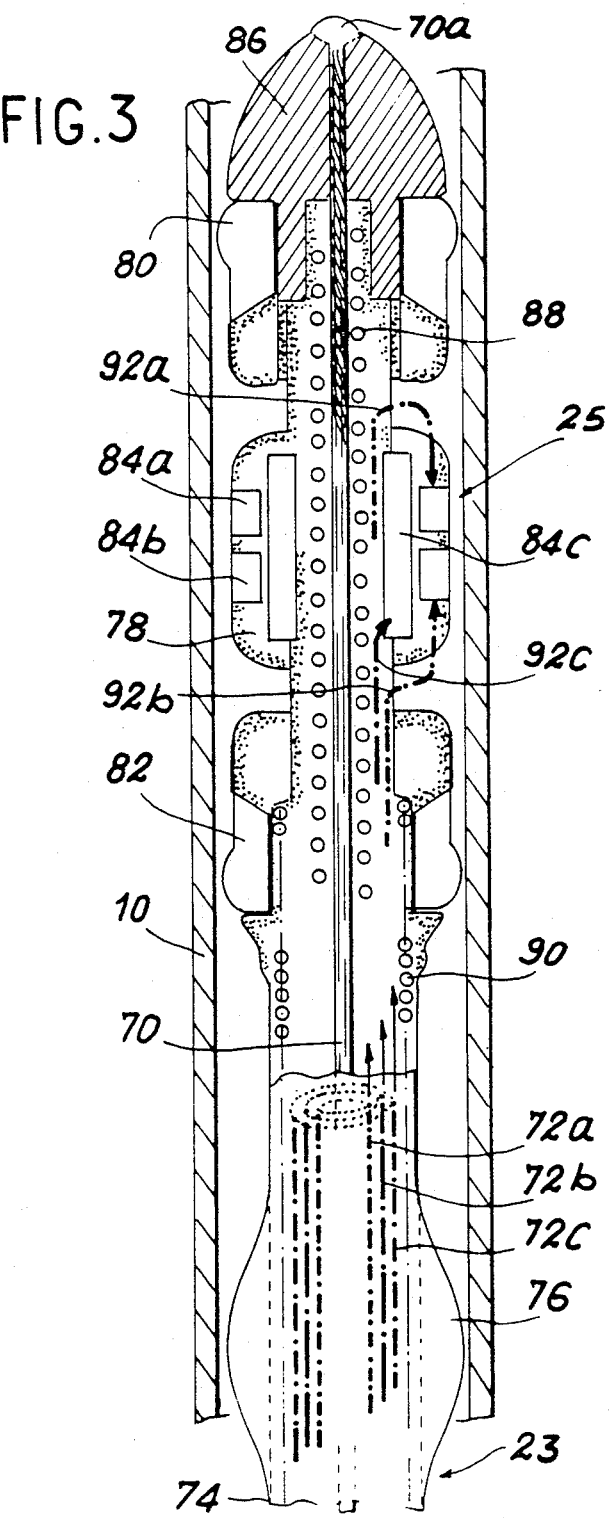
FIG. 3 is a view in longitudinal section, to an enlarged scale, of the end of the probe, showing the sensing head and its attachment to the end of the cable.

FIG. 3 shows how, in order to enable the sensing head 5 to return, even if certain parts of the cable 23 or of the connection between such cable and the measuring head should break, the pulling cable 70 of the cable 23 is continued inside the sensing head 25 as far as the ogival front end of the member 86, where the cable 70 is attached, for example, by a knot 70a glued with an adhesive such as Araldite (registered trade mark) to the nose of the member 86. The various fibres of the cable 70 are therefore coated with the adhesive, so that there is no risk that they will damage the internal walls of the tube 10.

Outside the pulling cable 70, the sensing head 25 is connected to the end of the cable 23 by means of a helical spring 90 attached at one and the same time to the resilient ring 82 and the first floater 76 of the cable. The connecting spring 90 contains the electrical connections between the coaxial conductors 72a, 72b and 72c of the cable and the conductors 92a, 92b and 92c electrically connected to the coils 84a, 84b and 84c of the sensing head. To prevent the probe from breaking at the level of this connection between the sensing head and the cable, the connecting spring 90 is preferably filled with resins, such as silicone resins, after assembly and the necessary checks have been carried out.

To ensure that the probe just described is introduced correctly—i.e., that the tensioning of the cable between the sensing head 25 and the pulley 50 is correct, even as the probe starts to be introduced, it is also proposed, as illustrated more particularly in FIG. 2, to change the pitch of the floaters 76 between the part of the cable nearest to the sensing head and the rest of the cable. By way of example, for a cable of 100 m, the floaters 76 can be separated by a step $p_1$ of 65 mm over the first ten meters, and then by a step $p_2$ of 130 mm over all the rest of the cable.

Of course, the introduction and return of the probe, and also the measurements corresponding thereto, can be performed automatically by means of adapted electronic circuits which do not form part of the invention. To this end, preferably a millimetric encoder is provided which can be associated more particularly with the electric motor controlling the rotation of the pulley 50, and a ball detecting device 94 can more particularly be disposed inside the sealing-tight envelope 16, on the part 20a of the connecting tube 20. The device according to the invention then operates as follows.

Referring again to FIG. 1, the valve 42 and the discharge valve 36 are closed, and the valve 34 and the discharge valve 44 are open. The compressor 30 is then pressurized until a pressure of about $10^5$ Pa is detected by manometer 38 at the inlet of the tube 10 to be checked. The motor associated with the pulley 50 is then put in operation, and also the torque motor 48, so that the probe 22 is progressively introduced into the tube to be checked with a constant imposed speed of movement of 0.4 meters per second.

It should be noted that in the absence of the speed-regulating device 26, the probe would be too quickly introduced into the tube, at an excessively variable speed to enable the desired check to be made.

At the same time the introduction pressure is stabilized at a value between 4 and 4.5 $10^5$ Pa.

When the probe is introduced over the desired length of tube, a length which can be determined in advance by means of a numerical display device, the compressor 30 and the electric motors are stopped and the device is deflated by opening the discharge valve 36. Basically, the probe is introduced over a length corresponding to the length of the tube to be checked minus a certain length which can be about one meter, so as to avoid damaging the diaphragms which are generally at the outlet from the tubes.

When the pressure at the inlet to the tube 10 has dropped to a value close to zero, the valve 42 is opened the valve 34 and the discharge valve 44 are closed, and the compressor 30 is restarted, so as to supply the total counterpressure to the tube for 4 to 5 seconds. The electric motors are then restarted to ensure the regular return of the probe. After about ten seconds the counterpressure is reduced to a value close to $2 \cdot 10^5$ Pa. Finally, when the ball detector signals the passage of the probe head, the device is completely stopped, and the probe-length-counting system is reset to zero.

In view of the regularity of the movement of the probe permitted by the invention, both during its introduction and its extraction, measurements can be performed either during the introduction of the probe, or during its extraction, or at one and the same time during these two operations. These measurements are carried out by means of conventional measuring systems which do not form part of the invention and will therefore not be described in detail.

Of course, security measures can be provided to prevent the deterioration of the probe cable and to stop its movement, more particularly when the pressure conditions and/or the speed of movement are not respected, and if the cable buckles. This latter condition can be detected by means of the ball detector and the millimetric encoder. It indicates that the probe has come out of the groove in the drive pulley.

As illustrated more particularly by FIG. 4, the device just described with reference to FIGS. 1 to 3 can be modified in various ways without exceeding the scope of the invention.

Figure 4:
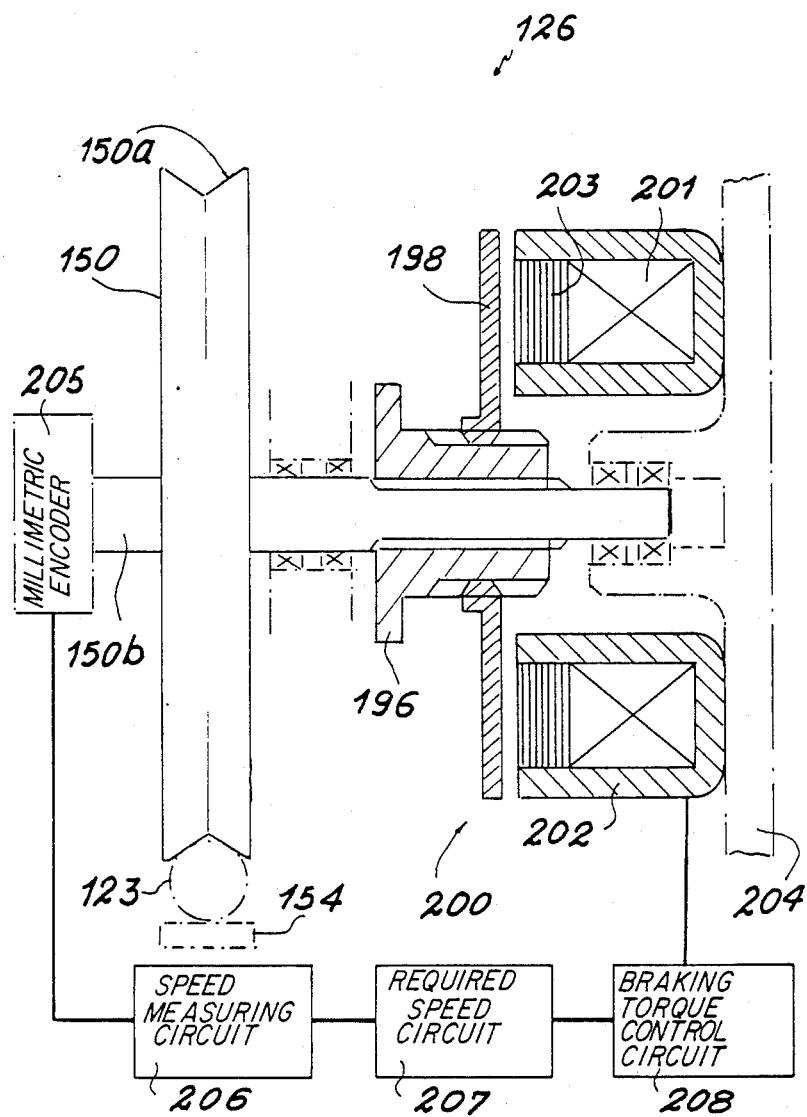
FIG. 4 is a sectional side elevation illustrating a second embodiment of the invention in which the speed of introduction of the probe is regulated by means of an electromagnetic brake connected for corotation to the shaft of the pulley over which the cable extends.

Thus, FIG. 4 shows a variant of the means for regulating the speed at which the probe is introduced into a tube to be checked. The regulating means 126 comprise, as before, a pulley 150 formed with a groove 150a over which the cable 123 passes. A belt device 154, similar to the device 52 in FIG. 2, enables the cable to be applied to the groove, whatever the section of the cable may be, as a result of the deformation of the belt 154.

In this embodiment, the shaft 150b of the pulley 150 has a grooved hub on which the armature 198 of an electromagnetic brake 200 is mounted. The brake 200 also comprises in known manner a coil 201 received in a magnetic circuit 202 open on the side of the armature 198 and having opposite the latter a friction lining 203. The coil 201, the circuit 202 and the lining 203 are mounted on a fixed support 204, coaxially with the shaft of the pulley.

The speed of movement of the cable is regulated by a millimetric encoder 205 which is disposed at the other end of the shaft 150b and whose signals are transmitted to a speed-measuring circuit 206. The speed of movement thus measured is compared with a required speed in a circuit 207. The circuit 207 delivers an error signal which is injected into a circuit 208 controlling the braking torque of the brake 200.

Finally, other decelerating systems might be used instead of the motor or the electromagnetic brake, such as an eddy-current brake or a hydraulic brake.

We claim:

1. Apparatus for inspecting curved tubes, such as helical heat exchanger tubes, comprising a sealed enclosure, a probe comprising a cable having floaters of larger diameter than the cable fixed thereto at lengthwise spaced intervals and having at a front end thereof a sensing head comprising electrical induction windings that are connectable with measuring apparatus by means of conductors extending along the cable, a rotatable cable winding means located within said enclosure to which the rear end of the cable is connected and about which the cable is normally coiled, connecting means through which said cable can pass for providing a sealed connection between said enclosure and one end of a tube to be inspected, and means for introducing into said enclosure a pressure fluid which flows through said connecting means and the tube to be inspected and is exhausted from the other end of said tube and whereby the probe is propelled through said tube from said one end thereof towards said other end, said apparatus being characterized by:
   A. a pulley confined to rotation in said enclosure at a location between said cable winding means and said connecting means and having a peripheral groove in which said cable is receivable;
   B. deceleration means for controlledly retarding rotation of said pulley to prevent its rotational speed from exceeding a predetermined value; and
   C. cable engaging means for maintaining the cable engaged in said groove in the pulley around a substantial portion of the periphery thereof so that the speed at which the probe is propelled through a tube to be inspected is controlled by the speed at which the pulley is permitted to rotate, said cable engaging means comprising
   (1) an endless belt,
   (2) a plurality of rollers about which said belt is trained and which are arranged to define a stretch of the belt that embraces said portion of the periphery of the pulley and engages the cable at the side thereof that is opposite the pulley, and
   (3) means for maintaining said stretch of the belt under yielding lengthwise tension that accommodates passage of floaters between the belt and the pulley.

2. Apparatus according to claim 1, wherein the deceleration means comprises a motor with electronically controlled speed.

3. Apparatus according to claim 1, wherein the deceleration means comprises an electromagnetic brake whose braking torque is controlled electronically.

4. Apparatus according to claim 1, further characterized by: motion transmitting means connected between said pulley and one of said rollers about which the belt is trained, whereby said roller is constrained to rotate at a speed which is dependent upon the rotational speed of the pulley and which causes said stretch of the belt to move at the same speed as the periphery of the pulley.

5. Apparatus according to claim 1, further characterized in that: said cable winding means is connected with the shaft of a torque motor to maintain yielding tension upon the cable as it is uncoiled from the cable winding means.

6. The apparatus of claim 1 wherein the floaters nearer said front end of the cable are spaced apart by shorter lengthwise intervals than the remainder of the floaters.

7. The apparatus of claim 6 wherein the length of said lengthwise intervals between said floaters nearer the front of the cable is substantially half that of the lengthwise intervals between the remainder of the floaters.

8. The apparatus of claim 1 wherein said cable comprises a central tension supporting cable which extends through the sensing head and is attached to the front end thereof.

9. Apparatus according to claim 8, wherein the central cable is attached to the front end of the sensing head by means of a knot coated with a gluing material.

10. A device according to claim 1, wherein the sensing head is connected to the cable via a connecting spring in which electrical connections are made between coaxial electric conductors of the cable and windings of the sensing head, said spring being filled with a filling material.

11. Apparatus according to claim 1 wherein the cable comprises an insulating sheath on to which the floaters are moulded.

* * * * *